United States Patent
Reimer et al.

(10) Patent No.: US 9,038,442 B2
(45) Date of Patent: May 26, 2015

(54) SYSTEMS AND METHODS OF DETERMINING A QUALITY AND A QUANTITY OF A FLUID

(71) Applicant: SSI TECHNOLOGIES, INC., Janesville, WI (US)

(72) Inventors: Lawrence B. Reimer, Georgetown, SC (US); Gregory P. Murphy, Janesville, WI (US)

(73) Assignee: SSI TECHNOLOGIES, INC., Janesville, WI (US)

(*) Notice: Subject to any disclaimer, the term of this patent is extended or adjusted under 35 U.S.C. 154(b) by 0 days.

(21) Appl. No.: 14/286,572

(22) Filed: May 23, 2014

(65) Prior Publication Data
US 2014/0250986 A1  Sep. 11, 2014

Related U.S. Application Data

(63) Continuation of application No. 13/294,866, filed on Nov. 11, 2011, now Pat. No. 8,733,153.

(60) Provisional application No. 61/412,667, filed on Nov. 11, 2010.

(51) Int. Cl.
*G01N 30/76* (2006.01)
*G01N 29/032* (2006.01)
(Continued)

(52) U.S. Cl.
CPC .......... *G01F 23/2962* (2013.01); *F01N 3/2066* (2013.01); *F01N 2610/1406* (2013.01); *G01F 23/2965* (2013.01); *G01F 25/0061* (2013.01); *G01N 29/024* (2013.01); *Y02T 10/24* (2013.01)

(58) Field of Classification Search
CPC ............ G01F 23/2962; G01F 23/2961; G01F 1/7082; G01F 23/2967; G01F 25/0061; G01N 29/024; G01N 2291/02818; G01N 29/02; G01H 5/00

USPC ............ 73/61.41–61.44, 61.49, 61.61, 64.53, 73/290 B, 290 R, 290 V
See application file for complete search history.

(56) References Cited

U.S. PATENT DOCUMENTS

| | | | |
|---|---|---|---|
| 4,391,149 A | 7/1983 | Herzl | |
| 4,571,693 A | 2/1986 | Birchak et al. | |

(Continued)

FOREIGN PATENT DOCUMENTS

| | | |
|---|---|---|
| DE | 10305003 | 8/2004 |
| DE | 102006013263 | 9/2007 |

(Continued)

OTHER PUBLICATIONS

PCT/US2011/060442 International Search Report and Written Opinion dated Feb. 7, 2012 (5 pages).

(Continued)

*Primary Examiner* — David A Rogers
(74) *Attorney, Agent, or Firm* — Michael Best & Friedrich LLP (57) ABSTRACT

A system for sensing a fluid. The system including a fixed object; a first transducer generating a first sound wave in a horizontal direction and to detect a first echo of the first sound wave from the fixed object; a second transducer generating a second sound wave in a vertical direction; a temperature sensor detecting a temperature of the fluid; and a controller. The controller configured to produce a first signal to drive the first transducer to produce the first sound wave, produce a second signal to drive the second transducer to produce the second sound wave, receive a first indication of the detected first echo, receive a second indication of the detected second echo, receive a temperature indication, determine a quality of the fluid based on the first indication and the temperature indication, and determine a quantity of the fluid based on the second indication.

26 Claims, 6 Drawing Sheets

(51) Int. Cl.
  *G01F 23/296* (2006.01)
  *F01N 3/20* (2006.01)
  *G01F 25/00* (2006.01)
  *G01N 29/024* (2006.01)

(56) References Cited

U.S. PATENT DOCUMENTS

| | | | |
|---|---|---|---|
| 4,773,267 A | 9/1988 | Abts | |
| 5,319,974 A | 6/1994 | Lenz | |
| 5,586,085 A | 12/1996 | Lichte | |
| 5,587,969 A | 12/1996 | Kroemer et al. | |
| 5,755,136 A | 5/1998 | Getman et al. | |
| 6,246,154 B1 | 6/2001 | Gluszyk et al. | |
| 6,279,378 B1 | 8/2001 | Sheen et al. | |
| 6,331,704 B1 | 12/2001 | Owen | |
| 6,484,088 B1 | 11/2002 | Reimer | |
| 6,545,946 B1 | 4/2003 | Huss et al. | |
| 6,573,732 B1 | 6/2003 | Reimer | |
| 6,691,025 B2 | 2/2004 | Reimer | |
| 7,114,390 B2 | 10/2006 | Lizon et al. | |
| 7,176,602 B2 | 2/2007 | Schlenke | |
| 7,542,870 B2 | 6/2009 | Reimer et al. | |
| 7,604,600 B2 | 10/2009 | Umemura et al. | |
| 7,775,092 B2 | 8/2010 | Murphy et al. | |
| 7,966,136 B2 | 6/2011 | Reimer et al. | |
| 8,184,290 B2 | 5/2012 | Hertens et al. | |
| 8,224,621 B2 | 7/2012 | Ajay et al. | |
| 8,302,472 B2 | 11/2012 | Rumpf | |
| 8,453,507 B2 | 6/2013 | Ellson et al. | |
| 8,464,583 B2 | 6/2013 | Sears et al. | |
| 8,733,153 B2 | 5/2014 | Reimer et al. | |
| 2002/0094582 A1 | 7/2002 | Williams et al. | |
| 2004/0093948 A1 | 5/2004 | Kelner et al. | |
| 2006/0173340 A1 | 8/2006 | Umemura | |
| 2007/0180903 A1 | 8/2007 | Gao | |
| 2008/0098824 A1 | 5/2008 | Bailey et al. | |
| 2008/0280371 A1 | 11/2008 | Anilkumar et al. | |
| 2009/0229341 A1 | 9/2009 | DiFoggio et al. | |
| 2010/0018309 A1 | 1/2010 | Marcovecchio et al. | |
| 2010/0126267 A1 | 5/2010 | Agam et al. | |
| 2014/0250986 A1 | 9/2014 | Reimer et al. | |

FOREIGN PATENT DOCUMENTS

| | | |
|---|---|---|
| EP | 102006013263 | 5/2007 |
| JP | H11-118774 A | 4/1994 |
| JP | 2002-131298 A | 5/2002 |
| JP | 2003-302386 A | 10/2003 |
| WO | 01/84086 | 11/2001 |

OTHER PUBLICATIONS

PCT/US2011/060442 International Preliminary Report on Patentability and Written Opinion of the International Searching Authority dated Apr. 14, 2013 (10 pages).
TULC Application Note Temperature Ultrasonic Level and Concentration Sensor for Urea, Diesel Exhaust Fluid (DEF), AdBlue Tanks, SSI Technologies, Inc., Dec. 14, 2012, Revision 2 (6 pages).
Office Action received in Japanese Patent Application No. 2013-538948, dated Feb. 2, 2015 (7 pages).

SYSTEMS AND METHODS OF DETERMINING A QUALITY AND A QUANTITY OF A FLUID

RELATED APPLICATIONS

This application claims the benefit of prior-filed U.S. Provisional Patent Application No. 61/412,667 filed on Nov. 11, 2010 and prior-filed U.S. patent application Ser. No. 13/294,866 filed on Nov. 11, 2011, the entire contents of which are hereby incorporated by reference.

BACKGROUND

The invention relates to systems and methods for determining the quality or concentration of a water based fluid and/or the depth of the fluid within a tank. Specifically, the invention relates to systems and methods for determining the quality and concentration of diesel exhaust fluid (DEF) contained within a tank and/or the depth of the DEF within the tank.

DEF is used to reduce nitrous oxide (NOx) gases in the exhaust of diesel engines. DEF is a mixture of purified water and 32.5% automotive grade UREA that is injected into the exhaust as a mist. The mist mixes with the exhaust and breaks down NOx in the exhaust into nitrogen, water, and carbon dioxide. When contaminants such as diesel fuel, water, ethylene glycol, etc. mix with the DEF, the ability of the DEF to reduce the NOx in the exhaust is diminished and/or irreversible damage may occur to the NOx reductant system.

DEF is stored in a tank of a vehicle and is injected into the exhaust at a ratio of about 1:50 to the diesel fuel being burned. A level of DEF in the tank is determined so as to provide an indication to a user when there is a need to add additional DEF.

SUMMARY

The invention uses immersed piezoelectric ultrasonic transducers to detect a level of DEF in a tank (e.g., to provide an indication to an operator of the quantity of DEF remaining), and to determine if the DEF has been contaminated (including determining the type and amount of contaminant). A concentration level of UREA within the DEF solution is also measured. An indication can be provided to a DEF control system of quality of the DEF fluid so a user can take remedial action if necessary.

In one embodiment, the invention provides a system including a tank, a controller, a transducer, and a temperature sensor. The temperature sensor senses a temperature of a fluid in the tank. The controller uses the sensed temperature to derive the temperature-dependent speed of sound for an ultrasonic signal traveling through the fluid. The controller generates a first command signal for the transducer. In response, the transducer generates an ultrasonic sound wave toward a fixed surface and receives an echo of the ultrasonic sound wave reflected off the fixed surface. The controller determines an elapsed time between the transmission of the ultrasonic sound wave by the transducer and the reception of the echo by the transducer. The controller also determines a concentration and presence of any contaminants in fluid in the tank based on the elapsed time and the sensed temperature of the fluid.

The controller also improves the quality of the received ultrasonic echo by modulating the amplitude of the transmitted ultrasonic sound wave. The controller modulates the ultrasonic sound wave by varying the amplitude and/or the number of voltage pulses of a command signal applied to the transducer. Preferably, the transducer is driven at resonance, where the frequency of the series of voltage pulses matches the transducer's temperature-dependent frequency characteristics. The controller may utilize a look-up table, including temperature based information, to generate the command signal.

The controller also determines if an ultrasonic echo is valid. An ultrasonic echo is determined to be valid when the echo is received within a predetermined time window. An echo is further determined to be valid when the amplitude of a signal representative of the echo is within a predetermined range. An echo is further determined to be valid when the duration of a signal representative of the echo is within a predetermined range. The controller generates at least one of an expected elapsed time window, an expected echo amplitude range, and an expected echo duration range.

The controller can record multiple echo reflections of a given ultrasonic transmission to increase the resolution of a recorded time measurement. In addition, information from the temperature sensor may be distributed to other devices and other locations through a communications module coupled to the controller.

In another embodiment, the invention provides a system including a tank, a controller, a transducer, and a temperature sensor. The temperature sensor senses a temperature of a fluid in the tank and provides an indication of the temperature to the controller. The controller uses the sensed temperature to derive a temperature-dependent speed of sound for an ultrasonic signal traveling through the fluid. The controller generates a first command signal for the transducer, detects a first echo signal from the transducer, and determines whether the transducer received the first echo signal within a near-field time. If the first echo signal was received within the near-field time, the controller detects a second echo signal having a magnitude within a predetermined range. If a second echo signal is not detected within a predetermined amount of time, the controller ignores the first echo signal, and generates a second command signal different than the first command signal. The controller modifies the second command signal until a second echo signal is detected. The controller converts either the first echo signal or the difference between the first echo signal and the second echo signal to a value representative of a distance to the target or a volumetric representation of the amount of fluid in the tank. To ensure that the controller can distinguish between a true echo signal and a secondary echo reflection, the controller is programmed to measure a ring time of the transducer by monitoring an output of the transducer continuously following a trigger command. The controller considers the ring time complete when the output signal is high for a predefined period of time. The controller is programmed to compensate for changes in temperature that can affect ring time and other measured variables, and determines the ring time of the transducer before making each measurement. The controller sets the near field time at about two and one-third times the ring time.

The controller also generates a command signal having multiple drive pulses which modulate the amplitude of the transmitted ultrasonic sound wave to optimize the quality of the received ultrasonic echo. Preferably, the transducer is driven at resonance with a series of pulses such that the frequency of the pulses matches the temperature-dependent frequency characteristics of the transducer. The controller may utilize a look-up table having temperature based data to generate the command signal.

The controller also determines if an ultrasonic echo is valid. An ultrasonic echo is determined to be valid when the echo is received within a predetermined time window, when the amplitude of a signal representative of the echo is within a predetermined range, and when the duration of a signal representative of the echo is within a predetermined range. The controller generates at least one of an expected elapsed time window, an expected echo amplitude range, and an expected echo duration range.

The controller also determines the plausibility of a contaminant having been introduced into the tank (e.g., during filling of the tank). The controller converts one of an elapsed time of a first echo signal and an elapsed time of a difference between the first echo signal and the second echo signal to a value representative of a distance to the target or a volumetric representation of an amount of fluid in the tank. The controller generates a fault output when the calculated distance or volume of the amount of fluid in the tank exceeds a capacity of the tank.

In one embodiment, the invention provides a system including a tank, a controller, two transducers, and a temperature sensor. The temperature sensor senses a temperature of a fluid in the tank, and the controller uses the sensed temperature to derive the temperature-dependent speed of sound for an ultrasonic signal traveling through a fluid in the tank. The controller generates a first command signal for the first transducer, causing the first transducer to generate an ultrasonic sound wave toward a fixed target submerged within the tank. The controller receives a series of echoes of the ultrasonic sound wave as the wave reflects off the fixed target back to the transducer. The sound wave bounces back and forth between the target and transducer multiple times. The controller determines an elapsed time between the transmission of the ultrasonic sound wave by the first transducer and the reception of the each reflected echo received by the first transducer. The controller also calculates the speed of sound for the ultrasonic wave traveling through the fluid using the elapsed time required for the reception of at least one of the reflected echoes and the sensed temperature of the fluid. Based on the calculated speed of sound and the sensed temperature of the fluid, the controller determines a concentration of the fluid and a presence of any contaminants within the fluid in the tank.

The controller generates a second command signal for the second transducer, and determines whether the second transducer receives an echo signal within a near-field time. If the echo signal is received within the near-field time, the controller detects a second echo signal of a predetermined magnitude from the second transducer. If the second echo signal is not detected within a predetermined amount of time, the controller ignores the first echo signal and generates a second command signal different than the first command signal. The controller modifies the second command signal until the second echo signal is detected. The controller uses either the time necessary to receive the first echo signal or the time difference between the first echo signal and the second echo signal to calculate a value representative of a distance to the target or a volumetric representation of an amount of fluid in the tank. To ensure that the controller can distinguish between a true echo signal and a secondary echo reflection, the controller is programmed to measure a ring time of the transducer by monitoring the output of the transducer continuously following a trigger command. The controller considers the ring time complete once a detect signal from the transducer is high for a predefined period of time. The temperature sensor is coupled to the controller and the controller is programmed to compensate for changes in temperature that can affect ring time and other measured variables. A communications module coupled to the controller distributes information from the temperature sensor to other devices and other locations. The controller determines the ring time of the transducer before making each measurement, setting the near field time being set at about two times the measured ring time.

The command signal includes multiple drive pulses which modulate the amplitude of the transmitted ultrasonic sound wave of both the first and second transducers. The controller modifies the command signal to optimize the quality of the received ultrasonic echoes from each transducer. Preferably, the transducers are driven at resonance, with a frequency of the series of pulses matching the temperature-dependent frequency characteristics of the transducer. The controller may utilize a look-up table having temperature based data to determine the characteristics of the command signal.

The controller also determines if ultrasonic echoes received from the first and second transducers are valid. An ultrasonic echo is determined to be valid when the echo is received within a predetermined time window. An echo is further determined to be valid when the number of received echo reflections is within a predetermined range. The controller generates at least one of an expected elapsed time window and an expected number of received echo reflections from the intended target.

The controller also determines a plausibility of a contaminant having been introduced into the tank, and generates a fault output should the calculated fluid level exceed the maximum capacity possible for DEF fluid within the tank.

The system is able to generate an accurate level measurement in the event of a temperature sensor failure. The controller determines a first elapsed time for the sound wave to travel from the first transducer to a fixed reflector and back. The controller also determines a second elapsed time for the sound wave to travel from the second transducer to a surface of the fluid in the tank and back. The controller calculates a depth of a fluid in the tank based on the ratio of the second elapsed time (level) to the first elapsed time (quality).

In another embodiment, the invention provides a system for determining a quality and/or a quantity of a fluid in a tank. The system includes a first transducer, a second transducer, a temperature sensor, and a controller. The first transducer is configured to generate a first sound wave and to detect an echo of the first sound wave. The second transducer is configured to generate a second sound wave and to detect an echo of the second sound wave, the second sound wave echoing off of a fixed structure a known distance from the second transducer. The temperature sensor is configured to detect a temperature of the fluid. The controller is coupled to the first transducer, the second transducer, and the temperature sensor, and has on-board diagnostics configured to detect an error condition based on an incorrect calculated speed of sound through the fluid, and generate a signal indicative of the error condition detected.

Other aspects of the invention will become apparent by consideration of the detailed description and accompanying drawings.

DETAILED DESCRIPTION

Before any embodiments of the invention are explained in detail, it is to be understood that the invention is not limited in its application to DEF or UREA based fluids and it is understood that the invention is not limited in its application to the details of construction and the arrangement of components set forth in the following description or illustrated in the following drawings. The invention is capable of other embodiments and of being practiced or of being carried out in various ways.

The level of DEF in a tank can be monitored by conventional methods including resistive float transducers, ultrasonic transducers (air-coupled), etc. Ultrasonic transducers emit a sound wave that reflects off a surface. The transducer acts as a receiver that receives the echo of the sound wave from the surface. Based on the time of flight of the sound wave to the surface and back, a controller determines, using the speed of sound, the distance to the surface. Because the speed of sound is constant in air (with some slight changes based on the temperature of the air), it is easy to perform the necessary calculations in an air-coupled transducer.

Alternatively, a fluid-coupled ultrasonic transducer can be used to monitor the quality and/or the level of the DEF within the tank. With a fluid-coupled transducer, the transducer is immersed in the fluid and positioned at the bottom of the tank. To determine the quality of DEF, ultrasonic sound waves are directed towards and reflected off of a fixed target immersed in the fluid. The sound waves generated by the transducer echo off of the fixed target (i.e., a reflector) which is located a known distance from the transducer and are detected by the transducer. To determine the level of DEF, the ultrasonic sound waves from the transducer are directed up towards the surface of the fluid. The sound waves generated by the transducer echo off the surface of the fluid and are detected by the transducer. This is similar to the air-coupled transducer with one caveat; the speed of sound varies greatly depending on the type of fluid and, to a lesser extent, the temperature of the fluid.

Figure 1:
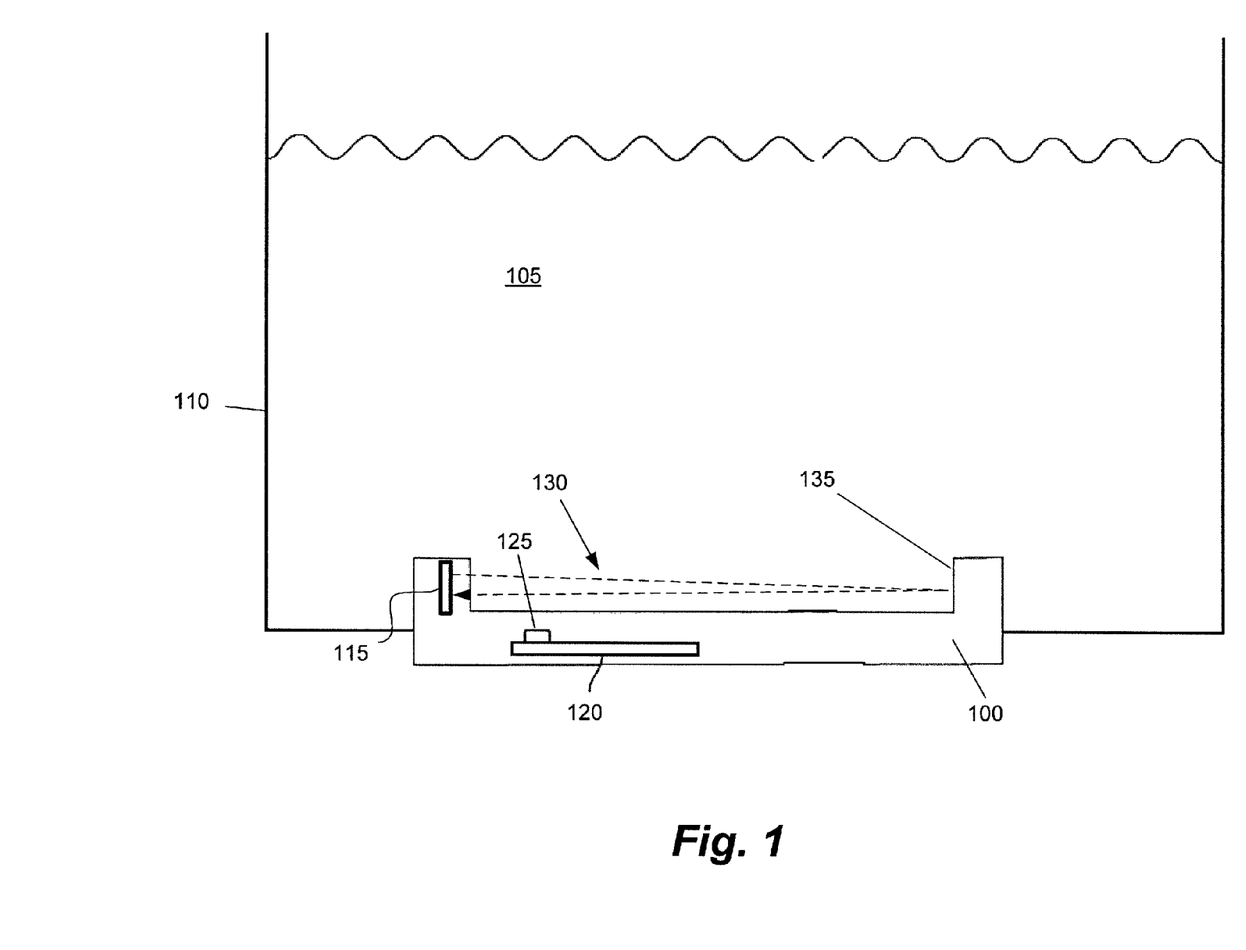
FIG. 1 is a diagram of a system for sensing the quality of the fluid within the DEF tank.

FIG. 1 shows a quality sensing system 100 for determining a quality of DEF 105 in a tank 110. The quality sensing system 100 includes a piezoelectric ultrasonic transducer 115, and a printed circuit board 120 having a temperature sensor 125 (e.g., a thermistor) and other components (not shown). The transducer 115 and the printed circuit board 120 are positioned at the bottom of the tank 110. The temperature sensor 125 is positioned such that the temperature sensor 125 detects the temperature of the DEF 105 in the tank 110. The transducer 115 acts as both a transmitter and a receiver. Ultrasonic sound waves 130 generated by the transducer 115 propagate through the fluid 105 and are reflected off of a reflector 135 back towards the transducer 115. The reflected ultrasonic sound wave 130 is detected by transducer 115, and reflects off the transducer 115 back towards the reflector 135. The ultrasonic sound wave 130 travels back and forth between the reflector 135 and the transducer 115 multiple times. The quality sensing system 100 can be integrated into the tank 110 or can be a separate assembly mounted in the tank 110.

Figure 2:
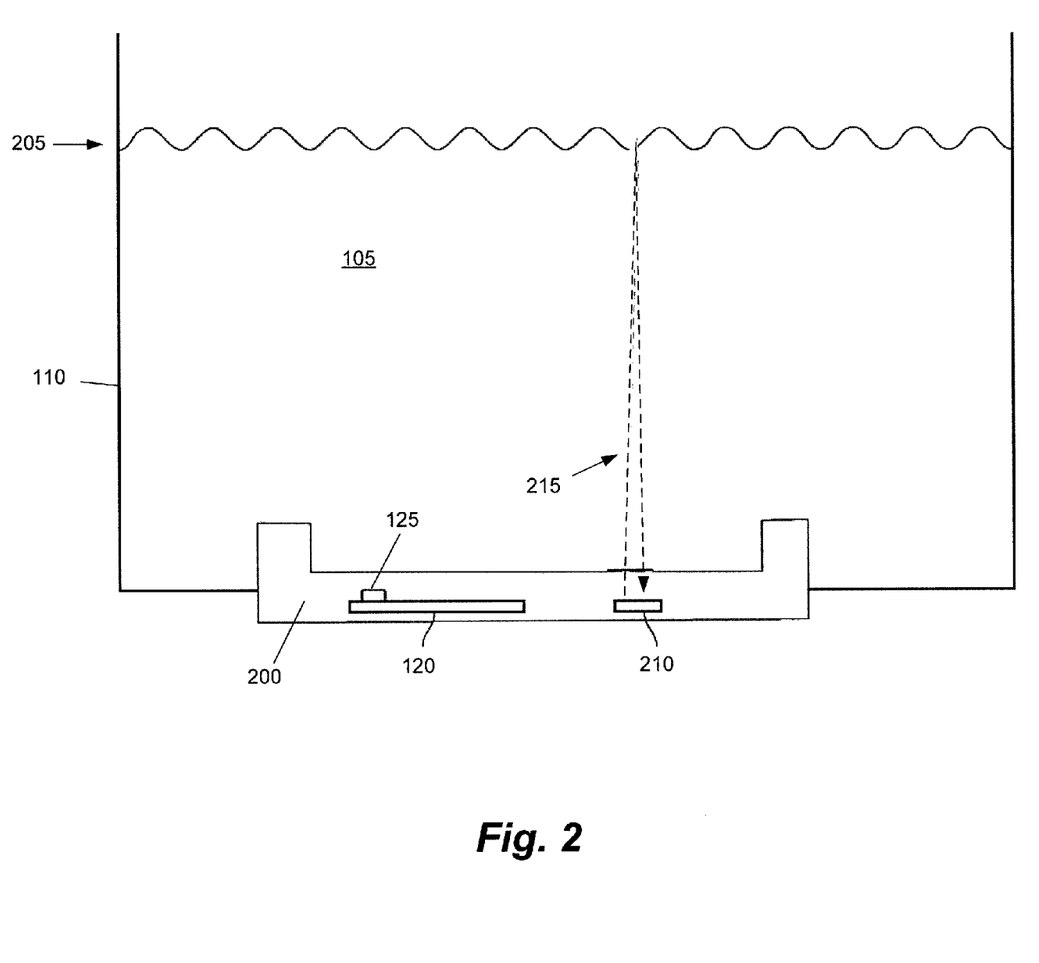
FIG. 2 is a diagram of a system for sensing the level of the fluid within the DEF tank

FIG. 2 shows a level sensing system 200 for determining a quantity of DEF 105 in a tank 110 by sensing a level of a surface 205 of the DEF 105 in the tank 110. The level sensing system 200 includes the same components as the quality sensing system 100 except that a piezoelectric ultrasonic transducer 210 is positioned at the bottom of the tank 110 such that ultrasonic sound waves 215 produced by the transducer 210 reflect off the surface 205 of the DEF 105 instead of a fixed reflector.

Figure 3:
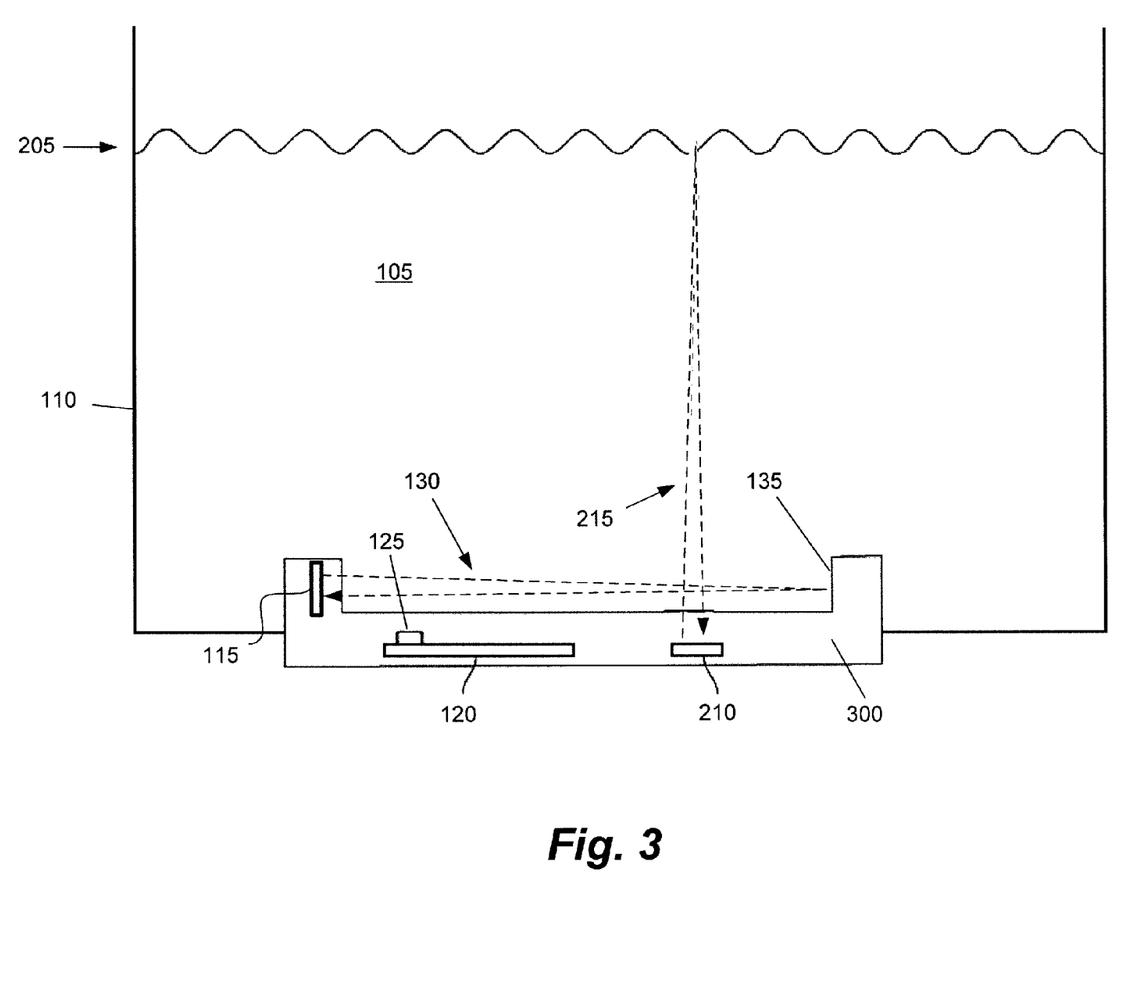
FIG. 3 is a diagram of a system for sensing the quality and the depth of DEF in a tank.

FIG. 3 shows a combination sensing system 300 for determining both a quality and a quantity of DEF 105 in a tank 110. The combination sensing system 300 includes two piezoelectric ultrasonic transducers 115 and 210. A quality transducer 115 is positioned to reflect ultrasonic sound waves 130 off a reflector 135 and a quantity (or level) transducer 210 is positioned to reflect ultrasonic sound waves 215 off a surface 205 of the DEF 105.

Figure 4:
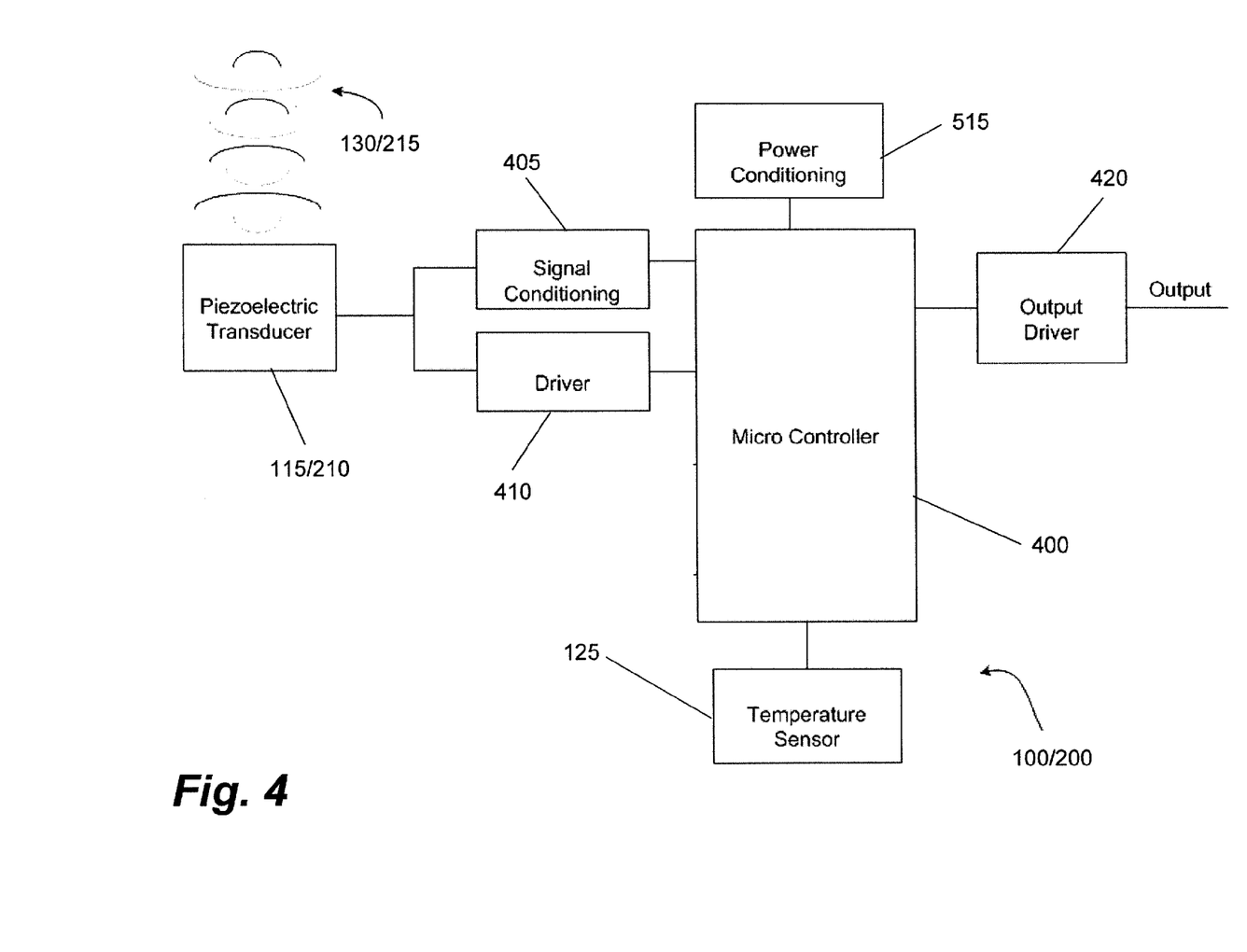
FIG. 4 is a block diagram of the systems of FIGS. 1 and 2.

FIG. 4 shows a block diagram of the quality sensing system 100 and the quantity sensing system 200. In addition to the transducer 115/210 and the temperature sensor 125, the system 100/200 includes a controller 400, a signal conditioning circuit 405, a driver 410, a power conditioning circuit 415, and an output driver 420. The controller 400 includes a processor (e.g., a microprocessor, microcontroller, ASIC, DSP, etc.) and memory (e.g., flash, ROM, RAM, EEPROM, etc.), which can be internal to the controller 400, external to the controller 400, or a combination thereof. One or more of the signal conditioning circuit 405, the driver 410, the temperature sensor 125, and the output driver 420 may be included in the controller 400. The transducer 115/210 operates in two modes, as a piezoelectric transmitter and as a piezoelectric receiver. When the transducer 115/210 is stimulated by an electric voltage at a resonant frequency of the piezoelectric crystals of the transducer 115/210, the transducer 115/210 emits the ultrasonic sound wave 130/215. When the transducer 115/210 is stimulated by an ultrasonic sound wave 130/215 (e.g., an echo) at a resonant frequency of transducer 115/210, the transducer 115/210 generates an output signal indicative of the sound wave. The signal conditioning circuit 405 serves to amplify and filter a low level signal received from the piezoelectric transducer 115/210 in response to being stimulated by a received ultrasonic sound wave 130/215.

Figure 5:
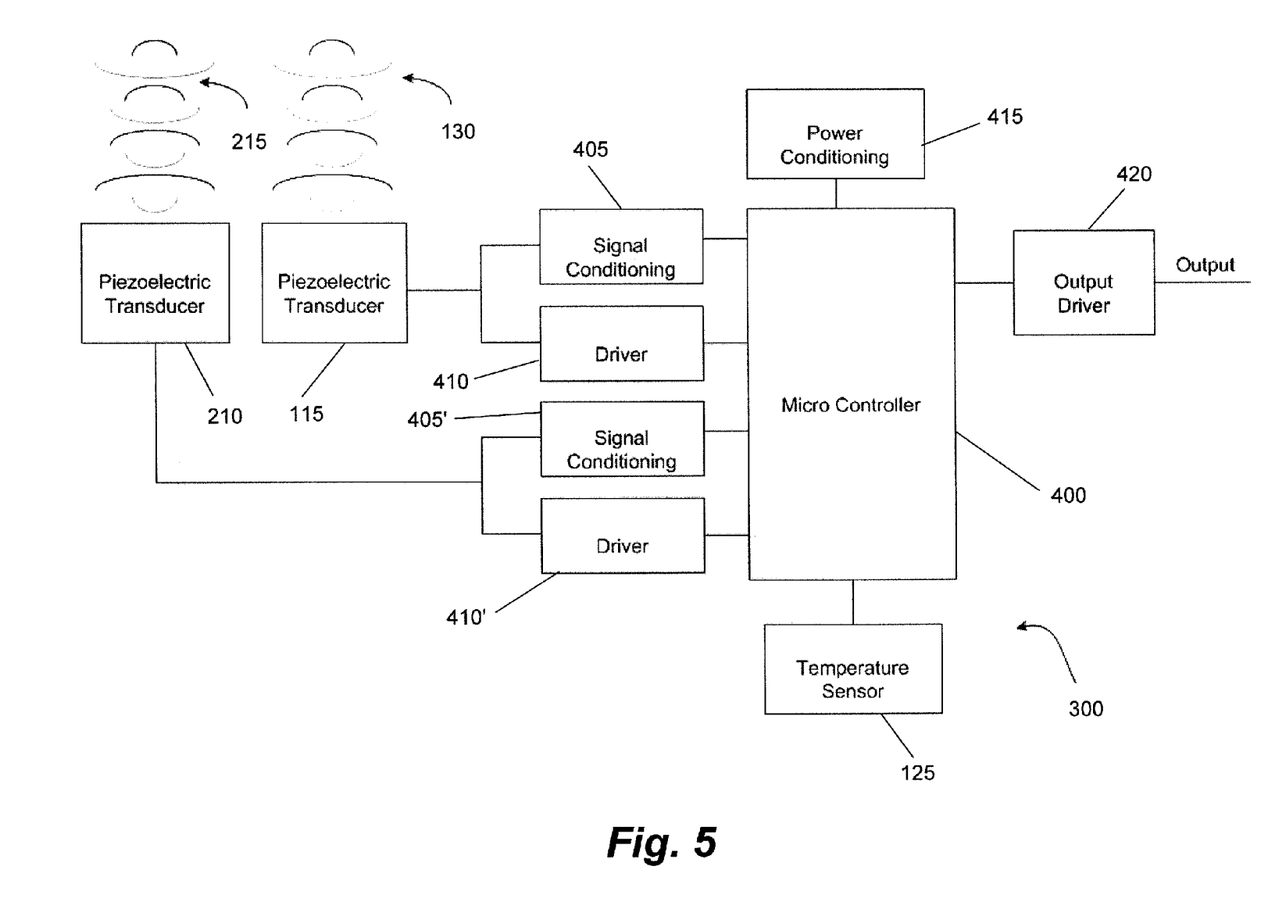
FIG. 5 is a block diagram of the system of FIG. 3.

FIG. 5 shows a block diagram of the combination sensing system 300. The system 300 includes a quality transducer 115, a level transducer 210 and the temperature sensor 125. The system 300 also includes a controller 400, a first signal conditioning circuit 405, a second signal conditioning circuit 405', a first driver 410, a second driver 410', a power conditioning circuit 415, and an output driver 420. The controller 400 includes a processor (e.g., a microprocessor, microcontroller, ASIC, DSP, etc.) and memory (e.g., flash, ROM, RAM, EEPROM, etc.), which can be internal to the controller 400, external to the controller 400, or a combination thereof. One or more of the signal conditioning circuits 405 and 405', the drivers 410 and 410', the temperature sensor 125, and the output driver 420 may be included in the controller 400. The transducers 115 and 210 operate in two modes, as a piezoelectric transmitter and as a piezoelectric receiver. When the transducers 115 and 210 are stimulated by an electric voltage at a resonant frequency of the piezoelectric crystals of the transducers 115 and 210, the transducers 115 and 210 emit the ultrasonic sound waves 130 and 215, respectively. When the transducers 115 and 210 are stimulated by ultrasonic sound waves 130 and 215, respectively, (e.g., an echo) at a resonant frequency of the transducer 115 and 210, the transducers 115 and 210 generate an output signal indicative of the received sound wave. The first signal conditioning circuit 405 serves to amplify and filter a low level signal received from the quality piezoelectric transducer 115 in response to being stimulated by a received echo from ultrasonic sound wave 130. The second signal conditioning circuit 405' serves to amplify and filter a low level signal received from the level piezoelectric transducer 210 in response to being stimulated by a received echo from ultrasonic sound wave 215.

In operation, the controller 400 sends a low level series of drive pulses and a drive pulse amplitude command signal to the driver 410. The drive pulses are at the resonant frequency of the transducer 115/210. The driver 410 amplifies the low level signal, applying a series of high voltage pulses to the transducer 115/210, causing the transducer 115/210 to emit the ultrasonic sound wave 130/215 at an amplitude proportional to the number of resonant drive pulses applied to the transducer 115/210. The ultrasonic sound wave 130/215 propagates through the fluid and is reflected off of the reflector 135 or the surface 205 back towards the transducer 115/210. The returned ultrasonic echo causes transducer 115/210 to resonate, creating a low level voltage signal which is amplified, filtered and shaped by signal conditioning circuit 405 and detected by the controller 400. The time necessary for the ultrasonic sound wave 130/215 to propagate through the DEF 105 from the transducer 115/210 to the reflector 135/surface 205 is stored in the memory of the controller 400 as a first echo reflection. Given sufficient amplitude, the ultrasonic sound wave 130/215 propagates back and forth between transducer 115/210 and the reflector 135/surface 205, creating a series of echo reflections. Typically 4 or 5 reflections are received for a given transmission. The reflections are measured and stored in the memory of the controller 400 for processing.

The number of echo reflections used by the system is dependent on the resolution required to discriminate between DEF concentration levels. For example if one echo reflection requires a first time to propagate through the fluid from transducer 115/210, reflect off of reflector 135 or surface 205, and return, a second echo reflection will require twice the first time to propagate, and a third echo reflection will require triple the first time, etc. Given this, two reflections provide twice the resolution of one reflection, three reflections provide three times the resolution, and so on. In a typical application, 4 to 5 reflections provide a good balance between the resolution required and the practical dimensions of sensor systems that can readily be assembled into a DEF tank.

When excited by the driver 410, the transducer 210 continues to resonate, or ring out, for a finite amount of time after the drive voltage has been removed. During this period of time the transducer 210 cannot be used as a receiver to detect an echo reflected off the surface 205 of the fluid 105, limiting the minimum fluid level that can be resolved by the capacity sensing system 200. Careful design can reduce the ring time but it cannot be eliminated entirely. An alternative approach for measuring the level of fluid in the tank when the tank is empty or nearly empty is to drive the level sensing transducer 210 with a large enough amplitude to create multiple reflections of the ultrasonic sound wave 215 between the surface 205 of the fluid 105 and the transducer 210 such that the ultrasonic sound wave 215 continues to reflect back and forth after the transducer 210 has stopped ringing. The time for the sound wave 215 to travel back and forth between the transducer and the surface 205 of the fluid 105 can then be calculated using a differential method, e.g., taking the time difference between two successive echo reflections.

The controller 400 generates a command signal which controls and modulates an amplitude of the ultrasonic sound wave 130/215 so as to achieve the desired number of echo reflections. The controller 400 performs this function by increasing or decreasing the number and/or amplitude of resonant voltage pulses applied to the temperature-dependent transducer. The number of resonant pulses applied to the transducer typically ranges from a low of 1 pulse to a high of 16 or more pulses, although other numbers of pulses may be applied. A switched capacitor charge pump is preferably used to increase or decrease the amplitude of the transducer drive voltage applied to the driver 410 under the control of controller 400. The drive voltage typically varies from low of 2 volts to a high of 30 volts. The number and amplitude of drive pulses is selected based on the number of echo reflections that are received. If the number of echo reflections falls below a preset quantity (calculated based on the relative distance being discerned), the controller 400 increases the amplitude and/or number of drive pulses. Conversely, if the number of echo reflections is greater than the preset quantity, the controller 400 decreases the amplitude and/or number of drive pulses applied to the transducer 115/210 (reducing unwanted distortion and noise). Thus, a closed loop gain control is created for the transmission and detection of the ultrasonic sound wave 130/215 echo reflections.

The controller 400 defines a near field operational mode as that which occurs when the first echo reflection identified occurs during a period of time equal to or slightly greater than twice the average ring time for the transducer 210. The controller 400 defines far field operational mode as that which occurs when the first echo reflection occurs outside of the time period defined by near field operational mode or, in other words, if the first echo reflection is received at a time interval greater than that of twice the average ring time for the transducer 210. In near field mode, the controller 400 modulates the power to the transducer 210 to ensure that at least two validated echo reflections are received following the conclusion of the ring period. In far field mode the controller 400 modulates the power to the transducer 210 to ensure that at least one valid echo reflection is received following the conclusion of the ring period.

The resonant frequency of a piezoelectric crystal, such as transducer 115/210, changes with temperature. The ability to modulate and control the amplitude of the ultrasonic wave 130/215 is dependent on driving the transducer 115/210 at its resonant frequency. The controller 400 performs this function by changing the frequency of the pulses applied to the transducer 115/210 based on the temperature sensed by the temperature sensor 125. The relationship between piezoelectric resonant frequency of the transducer 115/210 and temperature is specific to the selected type, size, shape, and mechanical design of the piezoelectric material. The temperature-dependent relationship is measured empirically for the design, and then is set forth in the form of a look-up table within the controller 400. Using a frequency specified in the look-up table for the measured temperature, the controller 400 selects and controls the transducer 115/210 drive frequency.

Ultrasonic waves 130/215 propagate throughout the tank 110, creating reflections off the walls of the tank 110 and other components submersed in the fluid. These reflections can interfere with the echo reflections from the reflector 135 and or surface 205. This can create false echo reflections that add to a string of recorded echo reflections or cancel a desired echo reflection within the string. In addition, movement of the fluid, temperature gradients, air bubbles, and other contaminants can interfere with the ultrasonic sound waves, creating shifts in time or generating noise within the received string of echoes. To ensure that the received echoes are not corrupted, the controller 400 validates a returned string of echoes by applying a window filter that checks a time for each returned echo against a known standard time along with a predetermined allowance for a change that can occur from one measurement to the next. The principle of the method is based on the fact that fluid properties change relatively slowly in comparison to the rate at which the measurements are being made. For example, during operation of a DEF system, except when the tank 110 is being filled, the level of fluid 105 in the tank 110 changes very slowly (e.g., over several minutes). In a practical implementation, measurements are made 20 times per second, whereas it takes tens of seconds for the properties of the fluid to change following a tank fill or the introduction of a contaminant. Therefore, parameters for an expected or allowable time window can be designed and applied to each returned echo time. The returned echo time is considered valid if it falls within the defined time window. Conversely, the returned echo time is considered invalid if it falls outside the defined time window. Invalid echo times are discarded by controller 400, while valid echoes are used to calculate the concentration of the DEF 105 present within the tank 110.

Figure 6:
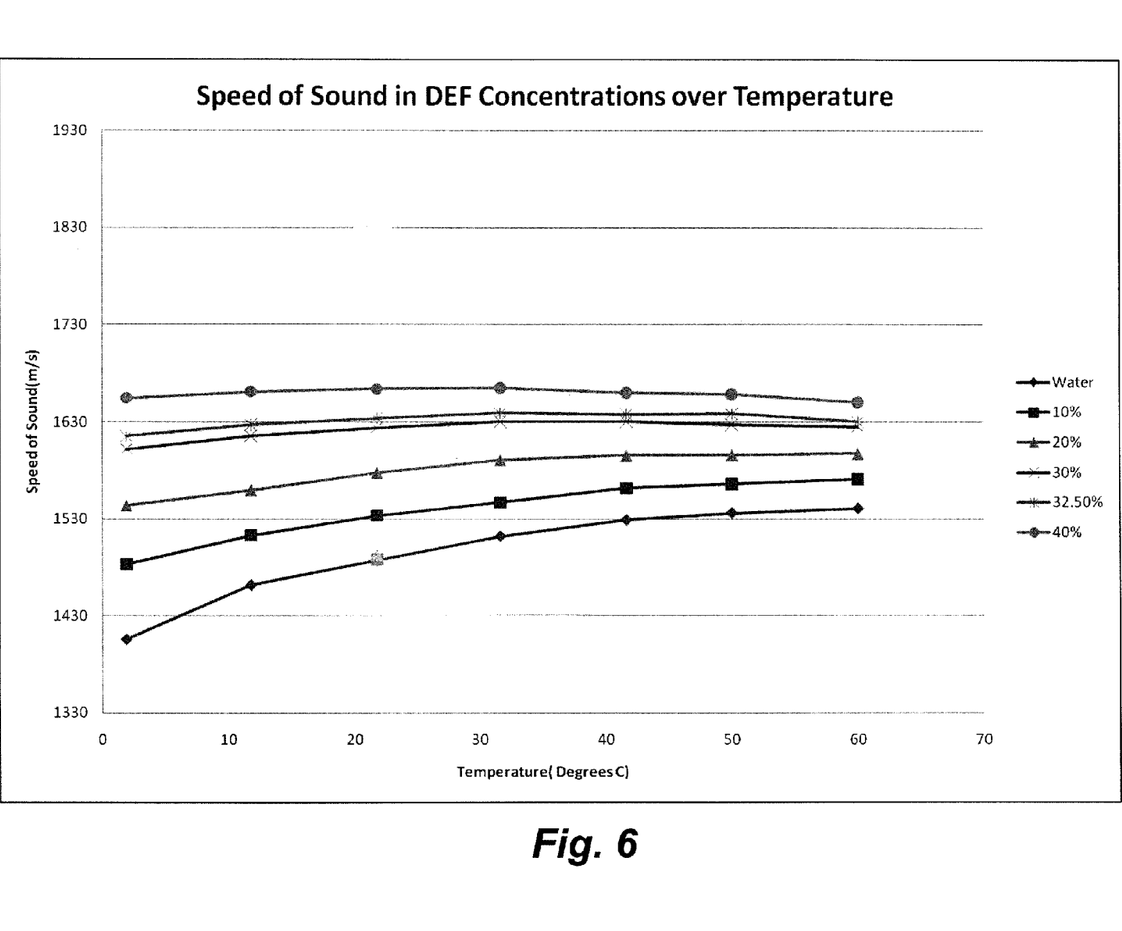
FIG. 6 is a chart of the speed of sound versus temperature for various DEF concentrations.

FIG. 6 shows a graph of the speed of sound versus temperature for a plurality of mixtures of automotive grade UREA and purified water (i.e., DEF). Based on the quantity of water versus UREA, and the temperature of the mixture, the speed of sound through the fluid can vary from about 1400 meters per second (m/scc) to about 1680 m/sec. in the quality sensing system 100 (and the combined sensing system 300), the physical distance between the transducer 115 and the reflector 135 is fixed. Therefore, the speed of sound, at a given temperature, through the fluid can be expressed by the relationship:

Speed of Sound $(T) = D \times N \times 2/T$, where where D is the distance between the transducer and the reflector,
T is the time measurement for the multiple echo reflection, and
N is the number of reflections.

Based on this formula, the controller 400 calculates the temperature-dependent speed of sound for the ultrasonic wave traveling through the DEF fluid, and then determines the concentration of the UREA solution by applying the calculated speed of sound and measured temperature to a look-up table such as that show in FIG. 6. As can be seen, using multiple reflections improves the resolution of the measurement by a factor equivalent to the number of reflections used. Alternatively, it is possible to create a look-up table using the data from FIG. 6 and known physical parameters of the sensor system 100, enabling the controller 400 to directly interpolate the fluid concentration from the table based on the measured temperature and the validated echo reflection time, for a given number of reflections. Use of a look-up table reduces the memory needed by the controller 400, and improves the processing speed of controller 400.

A digital or analog representation of the concentration of the fluid 105 is communicated from the controller 400 to the output driver 420, which conveys the measurements to an external controller for managing and controlling the function of a vehicle's DEF system. The output driver 420 may be in the form of a digital driver such as J1939 or CAN bus for communicating directly to the vehicle's data bus, or the output driver 420 may generate another suitable analog or digital signal, depending on the needs of the specific application.

It is possible for contaminants to become introduced into the tank (e.g., when filling the tank). Table 1 depicts the approximate speed of sound for a number of potential contaminants that could be introduced rather than the specified 32.5% UREA solution when filling a DEF system. As can be seen from Table 1 the speed of sound for common automotive liquids differs greatly from the DEF solution. Introduction of a contaminant into the tank 110 changes the speed of sound within the liquid 105, which is readily detected as either a shift in the UREA concentration level for small deviations, such as diluted UREA, or an out of range measurement for large deviations, such as would be the case with diesel fuel.

TABLE 1

| Contaminant | Speed of Sound (m/sec) |
|---|---|
| Diesel Fuel | 1350 |
| Brake Fluid | 1480 |
| Power Steering Fluid | 1480 |
| Purified Water | 1480 |
| Washer Fluid | 1590 |
| Ethylene Glycol | 1720 |
| Salt Water | 1830 |

Contaminants introduced into the DEF solution 105 can affect the ability of the DEF system to convert the NOx in the diesel exhaust to nitrogen, water, and carbon dioxide. Accordingly, it is desirable to determine if there are contaminants in the DEF, and what the contaminants are. The controller 400 can be configured to generate a diagnostic output, or out of range output signal, at output driver 420 whenever the measured speed of sound for a given temperature exceeds or falls below that which has been defined within the UREA concentration look-up table. Alternatively, the controller 400 can be used to selectively identify specific contaminants, such as diesel fuel, and then output the information in the form of a digital message, or to store the occurrence as a diagnostic event for future interrogation. In either case, the out of range output enables a DEF system can take action, shutting down the DEF system, or in certain cases disabling the vehicle, to prevent irreversible damage to DEF system components. The DEF system can also notify the user (e.g., lighting a tell tale light on a dashboard of a vehicle) if the quality of the UREA cannot sufficiently breakdown the NOx in the diesel exhaust. As used in the specification and claims, "contaminant" and "contamination" refer to the introduction of a contaminant into the UREA and also the dilution of the UREA (e.g., the introduction of water).

In the level sensing system 200 (and the combined sensing system 300), the physical distance between the transducer 210 and the surface 205 of the fluid 105 can be calculated based on the known speed of sound for the liquid and any mechanical offset that may exist between the transducer 210 and the bottom of the tank 110 as expressed by the relationship:

Level=Offset+Speed of Sound $(t) \times T/2$ where, Offset is the mechanical offset between the bottom of the tank 110 and the transducer 210,
Speed of Sound (t) is the temperature-dependent speed of sound for the fluid, and
T is the time measurement for the validated echo reflection.

Based on the quantity of water versus UREA in the DEF tank, and the temperature of the mixture, the speed of sound through the fluid can vary from approximately 1530 meters per second (m/sec) to about 1680 m/sec at room temperature (see FIG. 5 and Table 1). In normal operation the DEF system is operating with a UREA concentration level of 32.5% resulting in a speed of sound of 1630 m/sec at room temperature.

Controller 400 calculates the fluid level based on the known mechanical offset, the measured time for the echo reflection T, and the temperature-dependent speed of sound for the ultrasonic wave 215 traveling through the DEF fluid 105. A look-up table is preferably used to calculate the temperature-dependent speed of sound based on the measured temperature. Alternatively, it is possible to create a look-up table using the known physical parameters of sensor system 200 and the temperature-dependent speed of sound data for the fluid 105, enabling the controller 400 to directly interpolate the fluid level from the table based on the measured temperature and the validated echo reflection time T. Use of such a table reduces the memory space requirements and improves the processing speed of controller 400.

A digital or analog representation the level is communicated from the controller 400 to the output driver 420 to convey the measurements to an external controller for managing and controlling the function of the vehicle's DEF system. The output driver 420 may be in the form of a digital driver such as J1939 or CAN bus for communicating directly to the vehicle's data bus or the output driver 420 may generate another suitable analog or digital signal, depending on the needs of the specific application.

When contaminants become combined with the DEF 105, the speed of sound through the combined fluid can change drastically. It is possible for contaminants to become mixed with the DEF 105 prior to being introduced into the tank 110, or the contaminants could be introduced directly into the tank 110, mixing with the DEF 105. Many of the potential contaminants in Table 1 have speeds of sound which are in slower than that for DEF solution comprised of 32.5% UREA. Specifically, diesel fuel, brake fluid, power steering fluid, washer fluid, and water all have speeds of sound which are slower than the 1630 m/sec speed of sound associated with the 32.5% UREA solution. A slower speed of sound results in increased measurement times for the reflected echo over that which would have occurred for the specified DEF solution. Therefore if a contaminant was introduced when filling the tank then the level sensor system 200 would generate a level measurement in excess of the capacity of the tank 110. Knowing this the controller 400 can be programmed to perform a plausibility check to determine if a contaminant was introduced into the tank 110 by comparing the calculated level against the absolute physical capacity for the tank 110.

The controller 400 generates a diagnostic output or out of range output signal whenever the measured level exceeds the capacity of the UREA tank. This out of range output enables a DEF system controller to take action, shutting down the DEF system, or in certain cases disabling the vehicle, to prevent irreversible damage to DEF system components. The DEF system can also notify the user (e.g., lighting a tell tale light on a dashboard of a vehicle) if the quality of the UREA cannot sufficiently breakdown the NOx in the diesel exhaust.

The introduction of contaminants such as ethylene glycol and others which are more dense than the DEF fluid can stratify within the DEF tank 110 forming layers with the heavier contaminant covering the sensor system 300, and the lighter DEF layer forming up above. In such a case, the quality (concentration) measurement would reflect the properties of the contaminant, and the sensor system 300 would generate an appropriate output as previously described. Quality sensor system 100 would also detect the dense contaminant.

The introduction of contaminants such as diesel fuel, brake fluid, gasoline and others which are less dense than the DEF fluid can stratify within the DEF tank 110 forming layers with the heavier DEF fluid layer covering the sensor system 300, and the lighter contaminant layer forming up above. In such a case the concentration measurement generated by the quality sensing transducer 115 would look normal, whereas the level measurement from level sensing transducer 210 would suggest a much higher level of DEF 105, due to the longer travel time for the sound wave passing through the less dense contaminant layer. A slower speed of sound results in increased measurement times for the reflected echo over that which would have occurred for the specified DEF solution. Therefore, if a contaminant was introduced when filling the tank, the level sensing function would generate a level measurement in excess of the capacity of the tank 110. The controller 400, is programmed to perform a plausibility check to determine if the determined level exceeds the maximum level in the tank 110. The controller 400 generates a diagnostic message or an out of range output signal through output driver 420 for the quality sensor output and/or the level sensor output whenever the measured level exceeds the capacity of the tank 110.

The out of range output enables the DEF system controller to take action and shut down the DEF system, or the vehicle, to prevent irreversible damage to DEF system components and in addition notify the user (e.g., lighting a tell tale light on a dashboard of a vehicle) if the quality of the UREA will not be able to sufficiently breakdown the NOx in the diesel exhaust.

The controller 400 can also identify the introduction of a contaminant during a tank fill, providing that the level of DEF fluid 105 remaining within the tank is sufficient to immerse the quality sensing transducer 115, and the contaminant being introduced into tank 110 is lighter than the DEF, as would be the case with diesel fuel, brake fluid, gasoline and others. In such a case the resulting mixture will stratify with heavier DEF forming a layer on the bottom of the tank and the contaminating fluid forming a layer above the DEF. The level calculation based on the ratio between the time for the echo reflection generated in the level mode of operation against the time for the echo reflection generated in the quality mode of operation will exceed the capacity of the tank due to the differing speeds of sound between the DEF layer used for the quality sensing time measurement and the DEF/contaminant mixture used for the level sensing time measurement.

The sensor system 300 includes on-board diagnostic functions enabling it to detect failures of various components of the system 300. For example, the system 300 determines that there is an error when it detects the concentration level of the UREA decreasing (i.e., becoming diluted) at the same time as the level of the UREA is decreasing. This can be caused when the speed of sound determined using the quality transducer 115 is slower than the actual speed of sound. When the system 300 determines that the UREA is being diluted, the calculated speed of sound increases. Because of the error in determining the speed of sound, it is possible that the tank 110 is being filled, causing the dilution of the UREA, but for the level determination to calculate that the level of UREA is actually decreasing. Because the UREA cannot become diluted when the level of the UREA is decreasing, the system 300 determines an error exists.

In addition, should the speed of sound determined using the quality transducer 115 be faster than the speed of sound actually is, the system 300 determines the level of UREA in the tank 110 is higher that it actually is. Upon the tank 110 being filled, there will be a point in which the calculated level will exceed the known actual maximum level. In such a case, the system 300 determines an error exists.

Following a failure of the temperature sensor 125, the sensor system 300 can continue to operate with reduced functionality. When the temperature sensor 125 fails, the controller 400 calculates fluid level based on the ratio of the time for the echo reflection generated in the level mode of operation (transducer 210) against the time for the echo reflection generated in the quality mode of operation (transducer 115).

Given that the quality function traverses a fixed known distance (e.g., to reflector 135), the controller can calculate the level of fluid by multiplying the distance between the quality sensing transducer 115 and reflector 135 by the calculated ratio of the received echo times.

Thus, the invention provides systems and methods for accurately determining the quality and, or depth of a liquid within a tank.

What is claimed is:

1. A system for determining a quality and a quantity of a fluid in a tank having a bottom, the system comprising:
   a fixed object;
   a first transducer configured to generate a first sound wave in a horizontal direction and to detect a first echo of the first sound wave from the fixed object, the first transducer configured to be positioned near the bottom of the tank, and the fixed object positioned a known distance away from the transducer;
   a second transducer configured to generate a second sound wave in a vertical direction and to detect a second echo of the second sound wave, the second transducer configured to be positioned near the bottom of the tank such that the second sound wave travels toward a surface of the fluid in the tank;
   a temperature sensor configured to detect a temperature of the fluid; and
   a controller configured to:
     produce a first signal to drive the first transducer to produce the first sound wave,
     produce a second signal to drive the second transducer to produce the second sound wave,
     receive a first indication of the detected first echo from the first transducer,
     receive a second indication of the detected second echo from the second transducer,
     receive a temperature indication of the fluid from the temperature sensor,
     determine a quality of the fluid based on the first indication and the temperature indication, and
     determine a quantity of the fluid based on the second indication.

2. The system of claim 1, wherein the controller is further configured to determine whether a contaminant exists in the fluid based on whether a dilution of the fluid is detected while a measured volume of the fluid decreases.

3. The system of claim 1, wherein the first transducer and the second transducer produce an ultrasonic sound wave.

4. The system of claim 1, wherein the controller determines that the detected first echo is valid when the detected first echo is received by the first transducer within a predetermined time limit, has an amplitude that falls within a predetermined range, has a duration within a predetermined time range, or a combination of the foregoing.

5. The system of claim 1, wherein the controller determines that the detected second is valid when the detected second echo is received by the second transducer within a predetermined time limit, has an amplitude that falls within a predetermined range, has a duration within a predetermined time range, or a combination of the foregoing.

6. The system of claim 1, wherein the fluid is a urea solution.

7. The system of claim 1, wherein the controller determines a speed of sound of the fluid based on the first indication and the temperature indication.

8. The system of claim 1, wherein determining the quality of the fluid includes determining a concentration of the fluid.

9. The system of claim 1, wherein determining the quantity of the fluid includes determining a level of the fluid.

10. A sensing system for sensing a fluid in a tank, the system comprising:
    a sensor housing;
    a fixed target;
    a first transducer configured to generate a first sound wave and to detect a first echo of the first sound wave from the fixed target, the first transducer positioned near the bottom of the tank, the fixed object positioned a known distance away from the transducer;
    a second transducer configured to generate a second sound wave and to detect a second echo of the second sound wave, the second transducer positioned to direct the second sound wave toward a surface of the fluid in the tank;
    a temperature sensor configured to detect a temperature of the fluid; and
    a controller configured to:
      produce a first signal to drive the first transducer to produce the first sound wave,
      produce a second signal to drive the second transducer to produce the second sound wave,
      receive a first indication of the detected first echo from the first transducer,
      receive a second indication of the detected second echo from the second transducer,
      receive a temperature indication of the temperature of the fluid from the temperature sensor,
      determine a quality of the fluid based on the first indication and the temperature indication, and
      determine a quantity of the fluid based on the second indication, and the temperature indication.

11. The system of claim 10, wherein the controller is further configured to determine whether a contaminant exists in the fluid based on whether a dilution of the fluid is detected while a measured volume of the fluid decreases.

12. The system of claim 10, wherein the first transducer and the second transducer produce an ultrasonic sound wave.

13. The system of claim 10, wherein the controller determines that the detected first echo is valid when the detected first echo is received by the first transducer within a predetermined time limit, has an amplitude that falls within a predetermined range, has a duration within a predetermined time range, or a combination of the foregoing.

14. The system of claim 10, wherein the controller determines that the detected second echo is valid when the detected second echo is received by the second transducer within a predetermined time limit, has an amplitude that falls within a predetermined range, has a duration within a predetermined time range, or a combination of the foregoing.

15. The system of claim 10, wherein the fluid is a urea solution.

16. The system of claim 10, wherein the controller determines a speed of sound of the fluid based on the first indication and the temperature indication.

17. The system of claim 10, wherein determining the quality of the fluid includes determining a concentration of the fluid.

18. The system of claim 10, wherein determining the quantity of the fluid includes determining a level of the fluid.

19. A method of sensing a fluid in a tank, the method comprising:
    generating a first sound wave in a horizontal direction;
    detecting an echo of the first sound wave from a fixed object positioned at a known location;

generating a second sound wave in a vertical direction such that the second sound wave travels toward a surface of the fluid in the tank;

detecting an echo of the second sound wave;

detecting a temperature of the fluid;

determining a quality of the fluid based on the echo of the first sound wave and the temperature; and determining a quantity of the fluid based on the echo of the second sound wave, and the temperature.

20. The method of claim 19, further comprising determining whether a contaminant exists in the fluid based on whether a dilution of the fluid is detected while a measured volume of the fluid decreases.

21. The method of claim 19, further comprising determining that the echo of the first sound wave is valid when the echo of the first sound wave is received within a predetermined time limit, has an amplitude that falls within a predetermined range, has a duration within a predetermined time range, or a combination of the foregoing.

22. The method of claim 19, further comprising determining that the echo of the second sound wave is valid when the echo of the second sound wave is received within a predetermined time limit, has an amplitude that falls within a predetermined range, has a duration within a predetermined time range, or a combination of the foregoing.

23. The method of claim 19, wherein the fluid is a urea solution.

24. The method of claim 19, further comprising determining a speed of sound of the fluid based on the echo of the first sound wave and the temperature.

25. The system of claim 19, wherein determining the quality of the fluid includes determining a concentration of the fluid.

26. The system of claim 19, wherein determining the quantity of the fluid includes determining a level of the fluid.

* * * * *